(12) United States Patent
Christenson et al.

(10) Patent No.: US 8,444,609 B2
(45) Date of Patent: May 21, 2013

(54) IMPLANTABLE THERAPEUTIC SUBSTANCE DELIVERY SYSTEM WITH CATHETER ACCESS PORT BLOCK AND METHOD OF USE

(75) Inventors: Steven R. Christenson, Coon Rapids, MN (US); Irfan Z. Ali, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1276 days.

(21) Appl. No.: 11/413,835

(22) Filed: Apr. 28, 2006

(65) Prior Publication Data
US 2007/0255236 A1 Nov. 1, 2007

(51) Int. Cl.
*A61M 37/00* (2006.01)
*A61M 1/00* (2006.01)

(52) U.S. Cl.
USPC ............... 604/288.02; 604/288.04; 604/149; 604/153

(58) Field of Classification Search
USPC .............. 604/93.01, 119–125, 131–134, 140, 604/149, 150–152, 154, 156, 159, 288.01–288.03, 288.06, 891.1
See application file for complete search history.

(56) References Cited

U.S. PATENT DOCUMENTS

| 2,331,557 | A | * | 10/1943 | Lorehn et al. | 251/191 |
|---|---|---|---|---|---|
| 2,381,888 | A | | 8/1945 | Agre | |
| 2,473,196 | A | | 6/1949 | Dannenberg | |
| 2,510,442 | A | * | 6/1950 | Volpin | 251/191 |
| 2,735,774 | A | | 2/1956 | Henn | |
| 4,573,994 | A | * | 3/1986 | Fischell et al. | 604/891.1 |
| 4,919,563 | A | * | 4/1990 | Stice | 404/6 |
| 5,328,465 | A | * | 7/1994 | Kratoska et al. | 604/288.02 |
| 5,503,630 | A | * | 4/1996 | Ensminger et al. | 604/288.03 |
| 5,758,667 | A | | 6/1998 | Slettenmark | |
| 5,957,890 | A | | 9/1999 | Mann et al. | |
| 5,993,414 | A | * | 11/1999 | Haller | 604/93.01 |
| 6,023,224 | A | * | 2/2000 | Meyvis | 340/545.1 |
| 6,293,922 | B1 | * | 9/2001 | Haase | 604/93.01 |
| 6,315,049 | B1 | * | 11/2001 | Hickey et al. | 166/375 |
| 6,319,226 | B1 | * | 11/2001 | Sherry | 604/93.01 |
| 6,635,049 | B1 | | 10/2003 | Robinson et al. | |
| 6,663,609 | B2 | * | 12/2003 | Williamson et al. | 604/288.01 |
| 6,740,076 | B2 | * | 5/2004 | Hoben et al. | 604/891.1 |

(Continued)

FOREIGN PATENT DOCUMENTS
FR 2788983 A1 8/2000

OTHER PUBLICATIONS
PCT Search Report mailed May 28, 2008; 8 pgs.

*Primary Examiner* — Kevin C Sirmons
*Assistant Examiner* — William Carpenter

(57) ABSTRACT

A system including an implantable delivery device having a housing, a reservoir, fill and catheter access ports, and a denial device. The housing maintains the fill port in fluid communication with the reservoir. The catheter access port includes a septum between an inlet and a well. The denial device includes a pin, a biasing element, and a solenoid. The pin is arranged to be movable between a first position in which the pin blocks passage of a needle into the well and a second position, with the biasing element biasing the pin to the first position. The solenoid is operatively coupled to the pin and provides an energized and de-energized states; in the energized state, the solenoid moves the pin from the first position to the second position to permit access to the well. An external controller effectuating clinician control over operation of the denial device is also provided.

23 Claims, 7 Drawing Sheets

U.S. PATENT DOCUMENTS

| | | |
|---|---|---|
| 6,805,687 B2 * | 10/2004 | Dextradeur et al. .......... 604/151 |
| 6,878,135 B1 | 4/2005 | Haller et al. |
| 7,148,798 B2 * | 12/2006 | Chapman ..................... 340/528 |
| 2004/0059315 A1 | 3/2004 | Erickson et al. |
| 2004/0078000 A1 | 4/2004 | Borchard et al. |
| 2004/0220553 A1 | 11/2004 | Olsen |
| 2005/0187515 A1 | 8/2005 | Varrichio et al. |
| 2005/0273082 A1 | 12/2005 | Olsen |
| 2005/0277912 A1 * | 12/2005 | John .......................... 604/890.1 |
| 2006/0009921 A1 | 1/2006 | Shelton et al. |
| 2006/0047270 A1 | 3/2006 | Shelton |
| 2006/0056998 A1 | 3/2006 | Gray et al. |
| 2006/0080654 A1 | 4/2006 | Shelton |

* cited by examiner

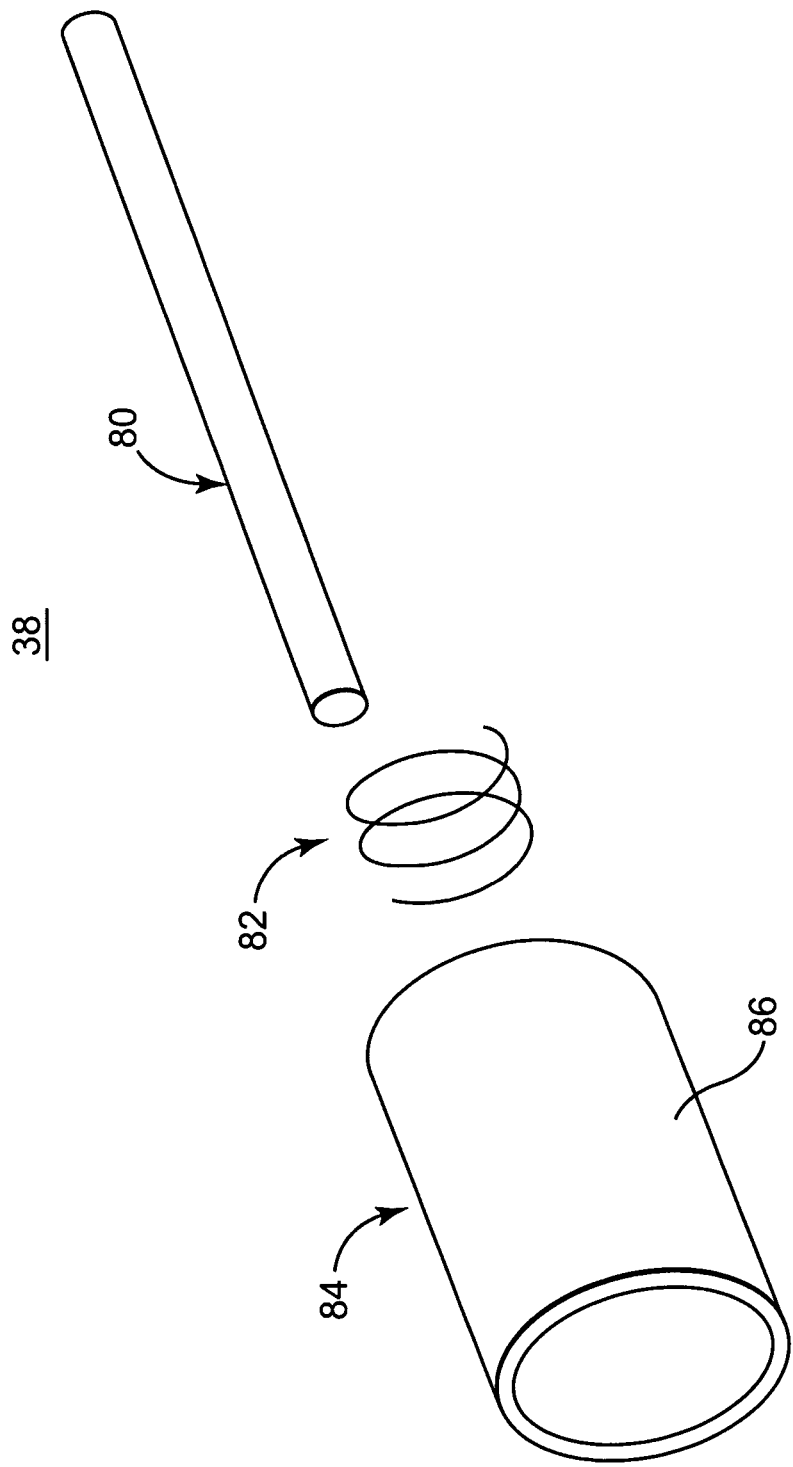

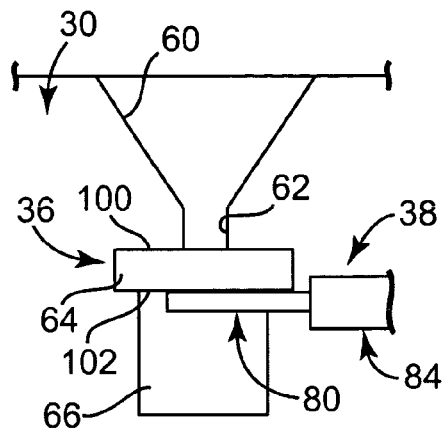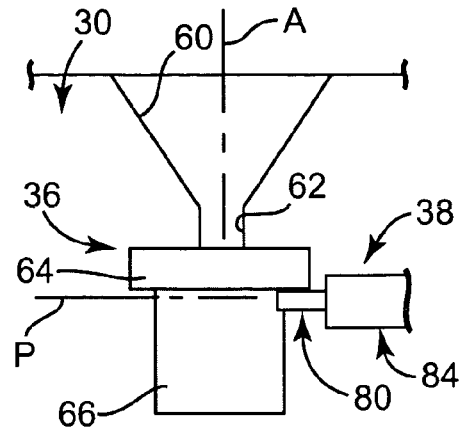
Fig. 5A  Fig. 5B
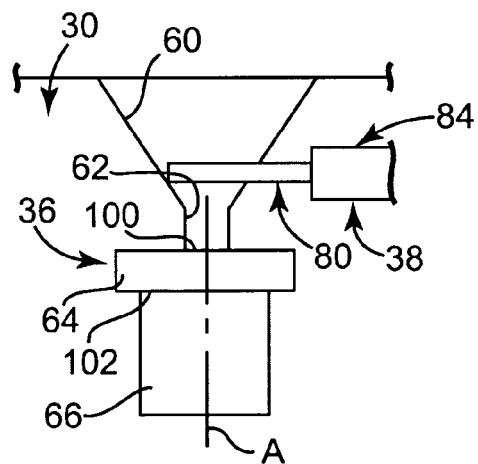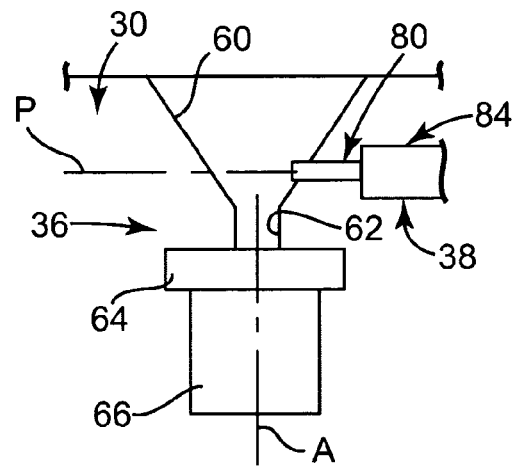
Fig. 6A  Fig. 6B

IMPLANTABLE THERAPEUTIC SUBSTANCE DELIVERY SYSTEM WITH CATHETER ACCESS PORT BLOCK AND METHOD OF USE

BACKGROUND OF THE INVENTION

The present invention relates to implantable medical devices for delivering a liquid therapeutic substance to a delivery site within a patient. More particularly, it relates to systems and methods for selectively blocking the catheter access port of an implantable therapeutic substance delivery device.

A variety of implantable medical devices are available for treating patients. For example, implantable therapeutic substance delivery devices are typically used to deliver infusion media or therapeutic substances (such as medication) to a patient at a regulated dosage. The implantable therapeutic substance delivery device (sometimes referred to as a drug pump or medicament pump) is implanted by a clinician into a patient at a location appropriate for the therapy. Typically, an infusion catheter is connected to a discharge outlet of the device, and is implanted/positioned to infuse the therapeutic substance at the desired therapy site so as to treat a condition such as pain, spasticity, cancer, neurodegenerative disease, trauma, etc. The term "implantable therapeutic substance delivery device" as used herein, refers to any device for delivering medicaments including, but not limited to, bladder pumps, accumulator pumps, fixed-rate bellows pumps, and the like.

In general terms, the implantable therapeutic substance delivery device commonly includes a drug reservoir containing a volume of the infusion media, along with a pumping mechanism to propel the infusion media in some metered or constant flow dosage to the desired delivery site from the reservoir via the catheter. Over time, the reservoir becomes depleted and it is necessary to refill the device with a new supply of the therapeutic substance. In order to avoid the need for surgery to access and refill the device, it is desirable to have the ability to percutaneously refill the drug reservoir. This is commonly achieved by providing the delivery device with a reservoir fill port that otherwise includes a resilient, resealable septum. The fill port is percutaneously accessible by introducing a hypodermic needle through the skin, to the fill port, and then through the septum, thereby forming a fluid connection between the needle and the drug reservoir. Implantable drug pump devices further commonly include one or more additional septum port(s), and in particular a catheter access port. The catheter access port is also accessible percutaneously via hypodermic needle, and provides direct access to the catheter, bypassing the pumping mechanism to allow the infusion of media directly into the patient, or removal of fluid from the patient (e.g., cerebral spinal fluid), via the catheter.

Although many clinicians view the catheter access port as highly desirable, others may be uncomfortable with its presence. In particular, a clinician desiring to refill the reservoir may mistakenly insert the refill needle into the catheter access port instead of the fill port. This can result in a relatively large volume of the drug being administered directly to the patient (i.e., the reservoir and pumping/metering device are bypassed and the refill volume of the drug is directly infused into the patient), potentially resulting in serious health problems for the patient. In light of this concern, efforts have been made to enhance the clinician's ability to distinguish the fill port from the catheter access port prior to, or simultaneously with, performing a percutaneous refilling procedure to better ensure that the correct port is accessed. For example, templates have been developed that facilitate the clinician's ability to visualize port locations relative to an exterior of the patient's skin. Further, screens or other needle denial devices can be placed across the catheter access port's opening; this configuration in combination with an appropriately sized refill needle can serve to prevent accidental insertion of the refill needle into the catheter access port. While fairly mechanically complex cam or rotor actuated port shields have been suggested in U.S. Pat. No. 6,805,687, such configurations may not be reliable during long-term use, and the systems described for controlling shield operation are less than optimal.

In light of the above, a need exists for improved devices, systems and methods for selectively restricting access by a needle to a catheter access port of an implantable therapeutic substance delivery device.

SUMMARY OF THE INVENTION

Aspects in accordance with principles of the present invention relate to a liquid therapeutic substance delivery system. The system comprises an implantable medical delivery device including a housing, a reservoir, a reservoir fill port, a catheter access port, and a denial device. The housing defines a catheter outlet, with the reservoir being maintained by the housing for containing the therapeutic substance. The reservoir fill port is fluidly connected to the reservoir to permit refilling of the reservoir. The catheter access port is provided apart from the reservoir fill port and is fluidly connected to the catheter outlet. In this regard, the catheter access port includes a needle inlet defining a passage, a well and a septum. The septum is disposed between the well and the needle inlet. Further, the well is fluidly coupled to catheter outlet via a fluid pathway such that the catheter access port provides fluid access to the catheter outlet from an exterior of the implantable delivery device. Finally, the denial device is associated with the catheter access port and includes a pin, a biasing element, and a solenoid. The pin is arranged to be linearly movable between a first position in which the pin blocks passage of a needle into the well and a second position. The biasing element biases the pin to the first position. The solenoid is operatively coupled to the pin and provides or operates in an energized state and a de-energized state. With this in mind, the solenoid is adapted and arranged such that in the energized state, the solenoid moves the pin from the first position to the second position. In some embodiments, the denial device is horizontally arranged, above or below the septum. In other embodiments, the denial device is vertically arranged below the septum. In yet other embodiments, the system further includes an external controller and a device controller, the combination of which are adapted to manage or control operation of the denial device in accordance with user-entered commands.

Other aspects in accordance with principles of the present invention relate to a method for restricting access to a well of a catheter access port in an implantable medical delivery device otherwise configured to delivery a therapeutic substance contained within a reservoir thereof to a delivery site of a patient. To this end, the implantable delivery device further includes a reservoir fill port apart from the catheter access port. The catheter access port, in turn, further includes a septum disposed between a needle inlet and the well. With this in mind, the method includes normally operating a solenoid in a de-energized state. In this regard, the solenoid is operatively coupled to a pin associated with the catheter access port to be moveable between a first position in which the pin blocks passage of a needle into the well, and a second position in which the pin does not block passage into the well. Further, a biasing element biases the pin to the first position, such that in the de-energized state, access to the well is restricted. The method further includes operating the solenoid in an energized state to transition the pin to the second position during times when access to the well is desired. In some embodiments, the method further includes performing an insertion routine in response to user-provided intent to insert a needle into the catheter access port. In one embodiment, the insertion routine includes operating the solenoid in the energized state for a predetermined period of time and then prompting the solenoid to return to the de-energized state if the presence of a needle is not detected in the catheter access port during the predetermined time period.

BRIEF DESCRIPTION OF THE DRAWINGS

FIG. 3 is a simplified, exploded view of one embodiment of a denial device useful with the implantable delivery device of FIGS. 2A and 2B;

FIGS. 5A and 5B are schematic illustrations of one arrangement of a denial device relative to a catheter access port in accordance with principles of the present invention and showing operation of the denial device;

FIGS. 6A and 6B are schematic illustrations of another arrangement of a denial device relative to a catheter access port in accordance with principles of the present invention and showing operation of the denial device.

DETAILED DESCRIPTION OF THE INVENTION

Figure 1:
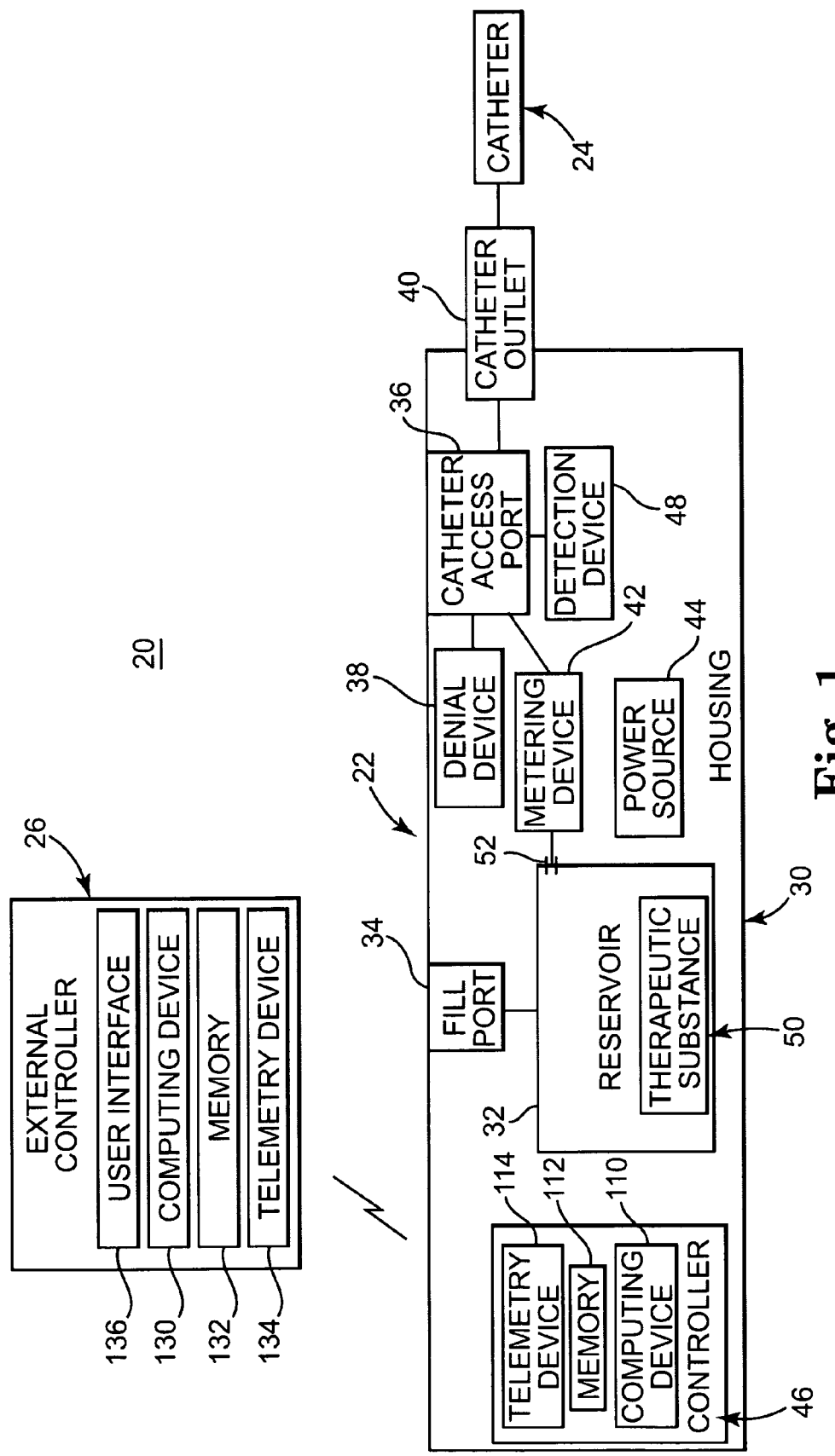
FIG. 1 is a block diagram of one embodiment therapeutic substance delivery system in accordance with principles of the present invention.

FIG. 1 shows one embodiment of a liquid therapeutic substance delivery system 20 in accordance with principles of the present invention in block form. The system 20 includes an implantable therapeutic substance delivery device 22 (also known as a drug pump), an implantable intrathecal catheter 24 and, in some embodiments, an external controller 26. Details on the various components are provided below. In general terms, however, the catheter 24 is typically implanted with the distal end thereof positioned at the desired therapeutic substance infusion site and a proximal end tunneled to the location where the delivery device 22 is to be implanted. The delivery device 22 is generally implanted subcutaneously beneath the skin where there is sufficient subcutaneous tissue to support the device 22. Once implanted, the delivery device 22 operates to infuse a therapeutic substance at a desired rate into the patient via the catheter 24. As is known in the art, the therapeutic substance is a product or substance intended to have a therapeutic effect, such as pharmaceutical compositions, genetic materials, biologics, and other substances. Other substances are intended to have a therapeutic effect yet are not easily classified such as saline solution, fluoroscopy agents, and the like. Regardless, the external controller 26 provides a clinician with the ability to interface with the delivery device 22 following implant. To this end, in some embodiments, the external controller 26 provides a clinician with the ability to perform a catheter access port insertion procedure as described below.

The implantable delivery device 22 can assume a variety of forms and generally includes a housing 30, a reservoir 32, a fill port assembly (or "fill port") 34, a catheter access port assembly (or "catheter access port") 36, and a denial device 38. The housing 30 maintains and/or forms the various components 32-38 and further forms or maintains a catheter outlet 40 adapted to be fluidly coupled to the catheter 24 as previously described. Apart from the denial device 38, the delivery device 22 can be akin to conventional drug pump configurations such as the SynchroMed® EL infusion system or the IsoMed™ constant flow infusion system, both available from Medtronic, Inc., of Minneapolis, Minn.; the Paradigm® insulin pump available from Medtronic-MiniMed, Inc., of Northridge, Calif.; etc; and thus can, in some embodiments, include additional components such as, for example, a metering device 42, a power source 44 (e.g., a battery), a device controller 46, etc. Unlike these and other conventional designs, however, the denial device 38 serves to selectively block access to the catheter access port assembly 36. In this regard, in some embodiments, the delivery device 22 further includes a detection device 48 for detecting or otherwise indicating whether a needle is present within the catheter access port assembly 36 in connection with operation of the denial device 38.

Figure 2A:
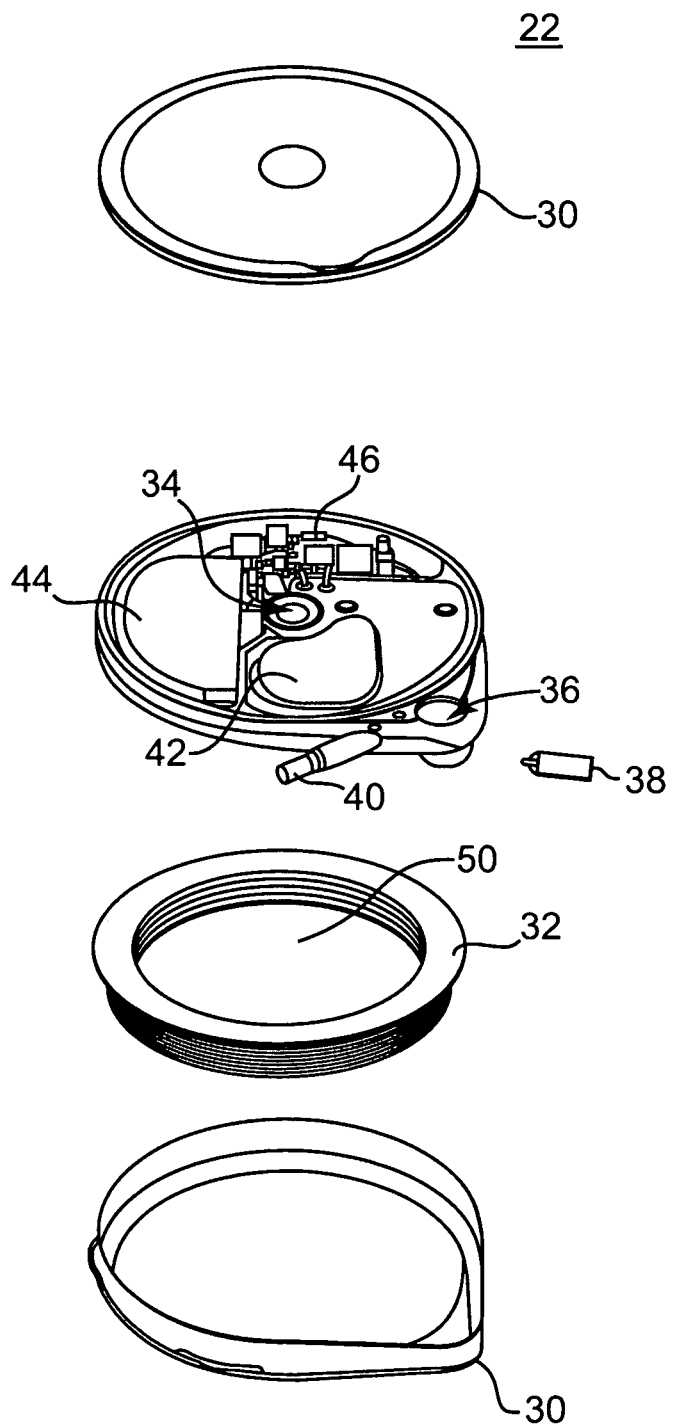
FIG. 2A is an exploded view of one embodiment implantable therapeutic substance delivery device in accordance with principles of the present invention useful with the system of FIG. 1.
Figure 2B:
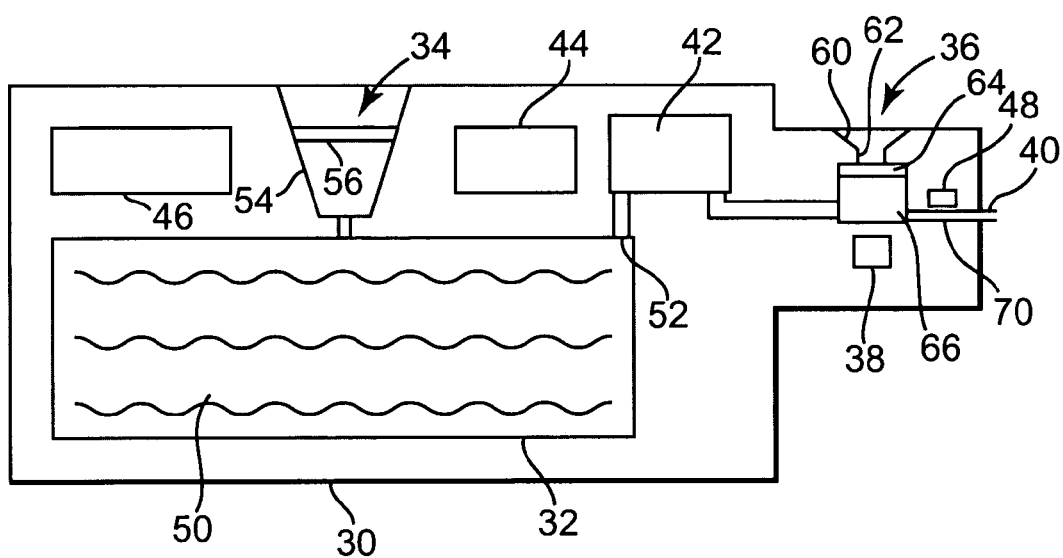
FIG. 2B is a schematic illustration of the device of FIG. 2A, with portions shown in block form.

In terms of general construction, and with reference to FIGS. 2A and 2B, the reservoir 32 is maintained by the housing 30 and is adapted for containing the liquid therapeutic substance 50 (illustrated generally in FIGS. 2A and 2B). The reservoir 32 forms a reservoir outlet 52 through which the contained therapeutic substance 50 is dispensed. Further, the reservoir 32 is fluidly connected to the fill port assembly 34 that otherwise facilitates filling of the reservoir 32 from a point exterior the housing 30. The fill port assembly 34 is of a type known in the art and generally includes a passage wall 54 across which a septum 56 is disposed.

The reservoir 32 can include or form a variety of structures or mechanisms useful to facilitate continuous, positive availability of the therapeutic substance 50 at the reservoir outlet 52, such as bellows acted upon by a propellant as is known in the art. Further, in some embodiments, the pumping and/or metering device 42 is provided as known in the art (collectively or individually referred to herein as a "metering device") to assist in directing or controlling flow of the therapeutic substance 50 from the reservoir outlet 52. In the one embodiment shown in FIG. 2B, the metering device 42 fluidly connects the reservoir outlet 52 with the catheter outlet 40, such that the therapeutic substance 50 from the reservoir 32 is dispensed from the delivery device 22 via the catheter outlet 40. In alternative embodiments, however, the reservoir outlet 52 can be fluidly connected to a separate or second discharge outlet that is not otherwise fluidly connected to the catheter outlet 40 (and thus the catheter access port assembly 36). In yet other alternative embodiments, the metering device 42 can be eliminated.

Similar to the fill port assembly 34, the catheter access port assembly 36 includes or forms a needle inlet 60 forming a passage 62, a septum 64, and a well 66. The needle inlet 60 provides a surface conducive to directing a needle tip (not shown) toward the passage 62. The septum 64 is a resilient, resealable material (e.g., silicone rubber), and is disposed between the passage 62 and the well 66, thus fluidly sealing the well 66 relative to the passage 62. Finally, the well 66 is sized to provide a bolus volume or region within with the needle tip can be located during a liquid exchange procedure, and is fluidly connected to the catheter outlet 40 via a fluid pathway 70 (FIG. 2B). With the one embodiment of FIG. 2B, the reservoir outlet 52 is also fluidly connected to the fluid pathway 70 (via, for example, the metering device 42), although in other embodiments, the therapeutic substance 50 is delivered from the reservoir outlet 52 along a separate fluid pathway as previously mentioned.

Embodiments of the denial device 38 are described in greater detail below, it being understood that a relationship/position of the denial device 38 relative to the catheter access port assembly 36 is illustrated in only general terms in FIGS. 2A and 2B. With this in mind, the denial device 38 is shown in greater detail in FIG. 3 and includes a pin 80, a biasing element 82 and a solenoid 84. The pin 80 is formed of a rigid material compatible with liquids expected to be introduced to or through the catheter access port assembly 36 (FIG. 2B), as well as to promote desired interaction with the solenoid 84 as described below (e.g., magnetic material). Further, the pin 80 is sized to form a partial or complete block to a portion of the catheter port assembly 36, again as described below. While the pin 80 is generally illustrated as being a straight cylinder, in other embodiments, the pin 80 can have other shapes and/or can include surface features that facilitate assembly of the denial device 38 (e.g., a flange for engaging the biasing element 82).

The biasing element 82 is, in one embodiment, a spring adapted for coupling to the pin 80 and/or the solenoid 84. Other forms are equally acceptable. Regardless, the biasing element 82 is configured to exert a biasing force on to the pin 80 at a level that can be overcome with operation of the solenoid 84.

The solenoid 84 is of a type known in the art, and includes a housing 86 maintaining one or more electrically conductive wire coils (not shown) that, when energized, creates a magnetic field. The solenoid 84 can include other features or constructions that facilitate assembly and/or operation of the denial device 38. Regardless, the solenoid 84 is characterized as being operable in an energized state in which an electrical current is delivered to the wire coil(s) to generate the magnetic field, and a de-energized state in which no current is delivered to the wire coil(s). In this regard, the solenoid 84 further includes external wiring (not shown) for delivering the electrical current to and from the wire coil(s).

Figure 4A:
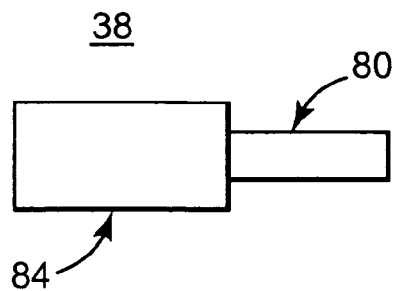
FIGS. 4A and 4B are simplified side views showing operation of the denial device of FIG. 3.
Figure 4B:
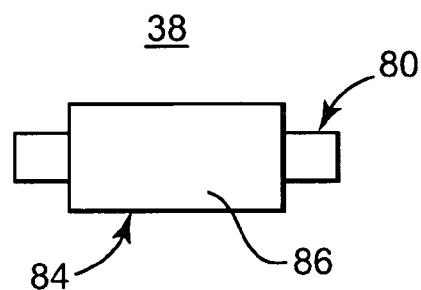

Upon final assembly, and with reference to FIG. 4A, the pin 80 is operatively coupled to the solenoid 84, with the biasing element 82 (hidden in the view of FIG. 4A) biasing to the pin 80 outwardly from the solenoid 84 to a first position when the solenoid 84 is in the de-energized state. Conversely, upon transitioning of the solenoid 84 to the energized state, the solenoid 84 exerts a magnetic field-induced force on to the pin 80 sufficient to overcome a force of the biasing element 82, thus drawing the pin 80 into the solenoid housing 86 to a second position as shown in FIG. 4B.

Figure 4C:
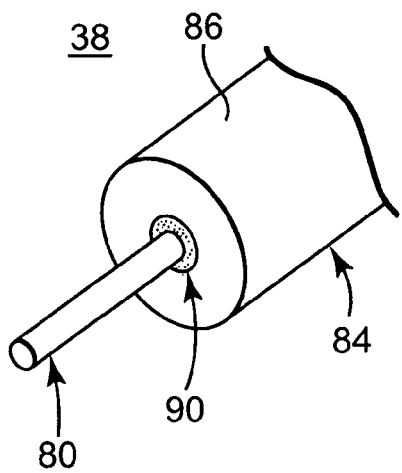
FIG. 4C is a simplified perspective view of a portion of an alternative denial device in accordance with principles of the present invention.
Figure 4D:
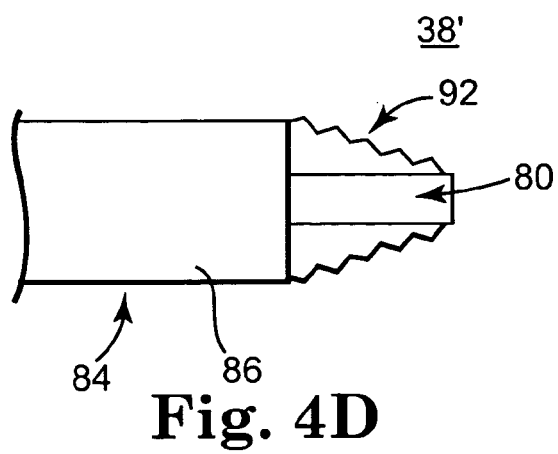
FIG. 4D is a simplified side view of a portion of another alternative embodiment denial device in accordance with principles of the present invention.

As described below, in at least the first position (FIG. 4A), the pin 80 will be exposed to liquids at or around the catheter access port assembly 36 (FIG. 2B). In fact, in some embodiments, a portion or an entirety of the solenoid 84 will also be temporarily or constantly exposed to liquids. With this in mind, in one embodiment the denial device 38 further includes an elastomeric seal 90 between the pin 80 and the solenoid housing 86 as shown in FIG. 4C. The elastomeric seal 90 serves to prevent liquids from passing between the pin 80 and the housing 86, and thus into the solenoid 84 (where deleterious interaction with the solenoid coils could occur). Alternatively and/or in addition, a hermetically welded barrier (not shown) can be provided that hermetically separates the pin 80 (and thus any liquids) from the coil(s) of the solenoid 84. A related alternative embodiment denial device 38' is shown in FIG. 4D whereby a bellows 92 is provided and forms a hermetic seal between the pin 80 and the solenoid housing 86. The bellows 92 has sufficient flexibility to permit the pin 80 to move between the first and second positions described above, and prevents liquids from passing into the solenoid 84 (and/or into contact with the solenoid coil(s)).

With the above description of the denial device 38 (FIGS. 4A-4C), 38' in mind, FIG. 5A illustrates one embodiment of the denial device 38 assembled relative to the catheter access port assembly 36 in accordance with principles of the present invention. More particularly, the denial device 38 is assembled within the housing 30, and is located below (relative to the orientation of FIG. 5A) the septum 64 in an off-set relationship relative to a central axis A (FIG. 5B) defined by the catheter access port assembly 36, and in particular the passage 62. In this regard, the septum 64 generally defines an outer surface 100 and an inner surface 102. The outer surface 100 faces the passage 62 (and is thus exposed relative to an exterior of the housing 30), whereas the inner surface 102 faces the well 66. With these conventions in mind, the denial device 38 is arranged such that in the pin 80 is in close proximity to the inner surface 102 of the septum 64 in the first position (i.e., the solenoid 84 in the de-energized state) of FIG. 5A. In the first position, then, the pin 80 blocks insertion of a needle (not shown) from or through the septum 64 and into the well 66. To this end, the pin 80 need not necessarily encompass an entirety of the inner surface 102; rather, the pin 80 need only be of a size commensurate with a size of the passage 62 (through which a needle will otherwise be inserted). In other embodiments, however, the pin 80 can have a larger size.

Where needle insertion into the catheter access port assembly 36, and in particular the well 66, is desired, the solenoid 84 can be operated in the energized state, causing the pin 80 to move to the second position in which the pin 80 no longer blocks the septum 64/well 66 interface as illustrated in FIG. 5B. As a point of reference, with the embodiment of FIGS. 5A and 5B, the pin 80 moves transversely (e.g., horizontally relative to the orientation of FIGS. 5A and 5B) relative to the central axis A in transitioning between the first and second positions, preferably along a pin axis P that otherwise intersects the central axis A (e.g., the pin 80 is, in some embodiments, transversely centered relative to the catheter access port assembly 36).

An alternative arrangement of the denial device 38 relative to the catheter access port assembly 36 in accordance with principles of the present invention is illustrated in FIG. 6A. In particular, the denial device 38 is assembled to the housing 30 at a location above (relative to the orientation of FIG. 6A) the septum 64 in an off-set relationship relative to the central axis A. Thus, the denial device 38 is arranged such that in the pin 80 is in closer proximity to the outer surface 100 of the septum 64 (as compared to the inner surface 102) in the first position (i.e., the solenoid 84 in the de-energized state) of FIG. 6A, it being understood that the denial device 38 can alternatively be arranged such that the pin 80 extends directly through the passage 62. In the first position, then, the pin 80 blocks insertion of a needle (not shown) from or through the needle inlet 60 and into the passage 62 (and thus into or through the septum 64 and the well 66). Once again, the pin 80 need not necessarily encompass an entirety of the needle inlet 60; rather, the pin 80 need only be of a size commensurate with a size of the passage 62 (through which a needle will otherwise be inserted). In other embodiments, however, the pin 80 can have a larger size.

Where needle insertion into the catheter access port assembly 36, and in particular the well 66, is desired, the solenoid 84 can be operated in the energized state, causing the pin 80 to move to the second position in which the pin 80 no longer blocks the passage 62 as illustrated in FIG. 6B. As a point of reference, with the embodiment of FIGS. 6A and 6B, the pin 80 moves transversely (e.g., horizontally relative to the orientation of FIGS. 6A and 6B) relative to the central axis A in transitioning between the first and second positions, preferably along a pin axis P that otherwise intersects the central axis A (e.g., the pin 80 is transversely centered relative to the catheter access port assembly 36).

Figure 7A:
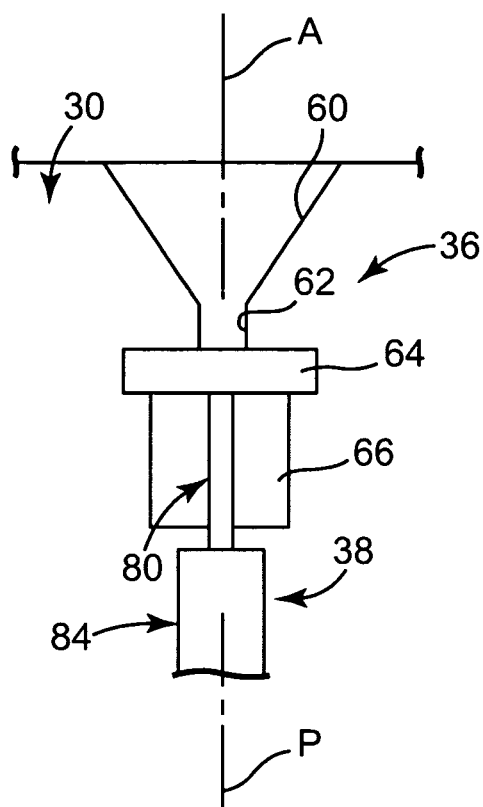
FIGS. 7A and 7B are schematic illustrations of another arrangement of a denial device relative to a catheter access port in accordance with the principles of the present invention and showing operation of the denial device.
Figure 7B:
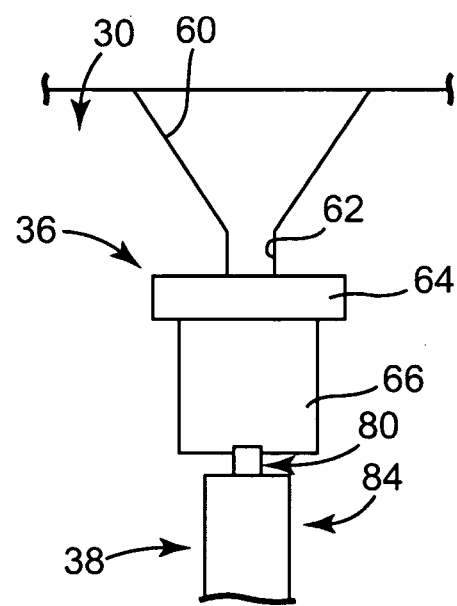

Yet another alternative arrangement of the denial device 38 relative to the catheter access port assembly 36 in accordance with principles of the present invention is illustrated in FIG. 7A. More particularly, the denial device 38 is assembled within or to the housing 30, and is located below (relative to the orientation of FIG. 7A) the septum 64 in a co-axially aligned relationship relative to the central axis A defined by the catheter access port assembly 36, and in particular the passage 62. In this regard, the denial device 38 is arranged such that the pin 80 is in close proximity to the inner surface 102 of the septum 64 in the first position (i.e., the solenoid 84 in the de-energized state) of FIG. 7A. In the first position, then, the pin 80 blocks insertion of a needle (not shown) from or through the septum 64 and into the well 66. Once again, the pin 80 need not necessarily encompass an entirety of the inner surface 102; rather, the pin 80 need only be of a size commensurate with a size of the passage 62 (through which a needle will otherwise be inserted). In other embodiments, however, the pin 80 can have a larger size.

Where needle insertion into the catheter access port assembly 36, and in particular the well 66, is desired, the solenoid 84 can be operated in the energized state, causing the pin 80 to move to the second position in which the pin 80 no longer blocks the septum 64/well 66 interface as illustrated in FIG. 7B. As a point of reference, with the embodiment of FIGS. 7A and 7B, the pin 80 moves co-axially (e.g., vertically relative to the orientation of FIGS. 7A and 7B) relative to the central axis A in transitioning between the first and second positions, along the pin axis P that is preferably co-axial with the central axis A (e.g., the pin 80 is, in some embodiments, transversely centered relative to the catheter access port assembly 36).

The one embodiment arrangement of FIGS. 7A and 7B can be of significant usefulness with conventional implantable delivery devices configurations that otherwise off-set the catheter access port assembly relative to a perimeter of the pump housing (e.g., the SynchroMed® Infusion Pump from Medtronic, Inc. and as generally shown in FIG. 2A). With these and other designs, the housing is conventionally of a reduced height in a region of the catheter access port assembly (as compared to a height of the housing in a region of the reservoir and/or pumping mechanism), providing substantial, unused space that is otherwise available for locating the denial device 38 as shown in FIGS. 7A and 7B. Alternatively, however, the arrangement of FIGS. 7A and 7B can be employed with a wide variety of delivery device housing configurations.

As indicated by the above, the denial device 38 is operable to selectively block access to the well 66 of the catheter access port assembly 36 via operation of the solenoid 84; the solenoid 84 must be energized (the energized state) to effectuate movement of the pin 80 to the second position that otherwise permits access to the well 66 such that the denial device 38 is characterized as "defaulting" to the first or blocked position. With this in mind, and returning to FIG. 1, in some embodiments the delivery device 22 is configured such that the device controller 46 effectuates control over and/or prompts operation of the solenoid 84, dictating whether the solenoid 84 operates in the energized state or the de-energized state. In further embodiments, the system 20 is adapted such that the external controller(s) 26 provides the device controller 46 with prompts or instructions relating to desired operation of the denial device 38 (e.g., operating the solenoid 84 in the energized or de-energized state). In still further embodiments, the needle detection device 48 provides additional information employed by the controller 26 and/or 46 in prompting operation of the solenoid 84.

In light of the above, in one embodiment, the device controller 46 can be of a type generally know in the art, and includes a computing device 110, a memory 112, and a telemetry device 114. The computing device 110 can be a microprocessor, state machine (Application Specific Integrated Circuit (ASIC) state machine), gate array, etc. as known in the art. The memory 112 can also be of any type known in the art, and may be provided as part of the computing device 112. Finally, the telemetry device 114 can assume any form appropriate for establishing wireless communication (e.g., RF, capacitive coupled, magnetic field, etc.) with a corresponding component of the external controller 26.

The external controller 26 can also be of a type known in the art, and generally includes a computing device 130 (preferably a microprocessor or microcontroller), a memory 132, and a telemetry device 134 similar to those described above with respect to the device controller 46, along with a user interface 136. The user interface 136 can assume a wide variety of forms including, for example, a user input device (such as a key board, touch screen, etc.) and a user output device (such as a display screen), and is electronically connected to the computing device 130 for transferring information or data between the components 130, 136. In one embodiment, the user interface 136 is akin to the N'Vision™ Programmer available from Medtronic, Inc. as part of the SynchroMed® Infusion System, although a wide variety of other forms are equally acceptable.

With the above configuration, the system 20 provides a user (not shown), such as a clinician, with the ability to prompt operation of the denial device 38 to permit access to the catheter access port assembly 36 when desired via the user interface 136. For example, with embodiments in which the denial device 38 defaults to the blocked state (i.e., the denial device 38 normally operates or defaults to the solenoid 84 being in the de-energized state such that the pin 80 is in the first position described above and thus blocks access to the well 66 as shown in FIGS. 5A-7B) and the user/clinician desires to percutaneously access the catheter access port assembly 36 with a needle, the solenoid 84 must first be prompted to operate in the energized state. Under these conditions, the user enters appropriate instructions or commands at the user interface 136 to indicate an intention to access the catheter access port assembly 36. In response, the external controller 26 (e.g., the computing device 130) prompts the signaling of information indicative of this user intent to the device controller 46 (via the telemetry devices 134, 114). The device controller 46, in turn, acts upon this signaled information, prompting the solenoid 84 to operate in the energized state such that the pin 80 moves to the second position to permit access to the well 66 of the catheter access port assembly 36.

In one embodiment, the computing device 110 of the device controller 46 is a microprocessor loaded or programmed with software adapted to process and act upon the user intent information (otherwise signaled from the external controller 26) in a desired fashion. Thus, in one embodiment, the software loaded or programmed to the delivery device 22 manages or controls operation of the denial device 38 (e.g., prompting operation of the solenoid 84 in a desired state) in opening or closing the catheter access port assembly 36. In a related, alternative embodiment, the computing device 110 of the device controller 46 is a hardware based state machine (e.g., ASIC state machine) adapted to process and act upon the user intent information signaled from the external controller 26, thus managing or controlling operation of the denial device 38/solenoid 84 in opening or closing the catheter access port assembly 36. In other embodiments, the external controller 26 effectively serves as the denial device 38 control processor, with the device controller 46 simply executing commands from the external controller 26 to operate the denial device 38 in a desired fashion.

Regardless of whether denial device 38 control/management originates in the external controller 26 or the device controller 46, in some embodiments in accordance with principles of the present invention, the system 20 is adapted to perform a catheter access port insertion routine upon learning that the user/clinician desires to access the catheter access port assembly 36 (e.g., via information or command(s) entered by the user/clinician at the user interface 136). In some embodiments, the insertion routine generally consists of prompting the solenoid 84 to operate in the energized state (e.g., transition from the default, de-energized state to the energized state) for a predetermined time period (e.g., a "procedure completion time period"). At the end of the port open time period, the insertion routine automatically blocks access to the catheter access port assembly 36 via prompting the solenoid 84 to return to or operate in the de-energized state. In this way, the catheter access port assembly 36 will not accidentally be left "open" or un-blocked for an extended period of time that might otherwise result in a subsequent, unintended insertion of a refill needle into the catheter access port assembly 36 during a reservoir refilling procedure.

In a related, alternative embodiment, the insertion routine comprises or further comprises the system 20 monitoring the catheter access port assembly 36 over a predetermined time period (e.g., a "monitoring time period") to determine, sense or estimate whether a needle has actually been inserted within the catheter access port assembly 36. If the presence of a needle is not detected or sensed by the expiration of the predetermined time period, the insertion routine results in prompting of the solenoid 84 to operate in the de-energized state, thus blocking the catheter access port assembly 36 as previously described. Alternatively, and/or in addition, the insertion routine includes blocking the catheter access port assembly 36 once a needle inserted into the catheter access port assembly 36 is removed (e.g., monitoring of the catheter access port assembly 36 indicates that the fluid exchange procedure is complete because the needle has been removed).

Along these same lines, in yet other embodiments, the system 20 is adapted such that a user can indicate at the user interface 136 that multiple needle insertions to the catheter access port assembly 36 will be performed as part of the particular liquid exchange procedures, with the insertion routine acting upon this information to not automatically block the catheter access port assembly 36 immediately after a needle insertion/needle removal is detected or determined. To this end, the insertion routine can operate to "count" or track the number of needle insertion/removals and correlate this with user-entered data relating to the number of insertion/removals the particular procedure will have before closing the catheter access port assembly 36 (via operation of the denial device 38), or can simply by-pass the automatic closing-with needle removal operational step (and instead, for example, block the catheter access port assembly 36 after a predetermined time period (e.g., the procedure completion time period) has expired).

In connection with the above insertion routine, the detection device 48 can be provided and employed to generate information indicative of the presence (and/or absence) of a needle within the catheter access port assembly 36. To this end, the detection device 48 can assume a wide variety of forms, for example as described in U.S. Publication Nos. 2004/0073196 (Adams, et al.) and 2005/0187515 (Varricho et al.), and U.S. Pat. Nos. 5,171,228 (McDonald) and 6,740,076 (Hoben et al.), the teachings of all of which are incorporated herein by reference. Regardless, the detection device 48 essentially monitors the catheter access port assembly 36 and signals information indicative of the presence (and/or absence) of a needle to the device controller 46 that, in turn, operates in accordance with the insertion routine as described above and/or signals the information to the external controller 26 (via telemetry devices 114, 134), with the external controller 26 processing and prompting action(s) implicated by the detection device 48 information.

Where the insertion routine includes both an "automatic catheter access port closure after a set time" and "catheter access port closure if needle presence is not detected" operational steps, the corresponding predetermined time periods (e.g., the procedure completion time period and the monitoring time period mentioned above) can be the same or different Regardless, in some embodiments, the predetermined time period(s) described above in connection with the insertion routines is or are a value(s) stored in the memory 112 associated with the device controller 46. In accordance with this approach, in further embodiments the system 20 is adapted such that a user can effectuate a change in the stored value(s) via appropriate commands or instructions entered at the user interface 136. Thus, for example, where the user prefers that the insertion routine operate the solenoid 84 in the energized state for a longer period of time than currently provided (e.g., the currently stored procedure completion value is five minutes, and the user desires a ten minute time period before closing or blocking of the catheter access port assembly 36 by the denial device 38), the user simply enters appropriate commands at interfaces with the user interface 136. In related embodiments, the predetermined time period(s) is or are a value(s) stored in the memory 132 of the external controller 26. With this approach, the system 20 can be configured such that each time the external controller 26 operates to effectuate the insertion routine, the stored value(s) is communicated to the device controller 46. Along these same lines, the external controller 26 can also be adapted or programmed to permit a user to alter the stored value(s) as previously described.

In yet another related embodiment, the system 20 can be adapted to provide the clinician with an advance warning that the catheter access port assembly 36 is about to be closed or blocked. The warning can be visual and/or audible, and can be provided at the user interface 136, by a sound generator (not shown) carried by the implantable delivery device 22, or both. Thus, for example, when the insertion routine dictates that the denial device 38 will be operated to block (as previously described) the catheter access port assembly 36 in the immediate future (e.g., in 30 seconds), the system 20 can operate to alert the clinician of this fact. In response, the clinician can confirm that the procedure in question will be completed prior to the closure operation, or can, in some embodiments described above, extend the time period before catheter access port assembly closure will occur by entering appropriate commands at the user interface 136.

In yet other embodiments, one or both of the external controller 36 and/or the device controller 46 can be adapted to log information (for example within the memory 112 and/or 132) relating to actions at the catheter access port assembly 36. The logged information is preferably date and/or time stamped to provide context for subsequent review, and can include one or more of an occurrence of the denial device 38 being in an open state (i.e., the solenoid 84 in the energized state) and a needle insertion detected at the catheter access port assembly 36; an occurrence of the denial device 38 being in the open state and a needle insertion is not detected at the catheter access port assembly 36 for a predetermined time period (e.g., the monitoring time period); an attempted needle insertion to the catheter access port assembly 36 is detected while the denial device 38 is in the closed or blocked state (i.e., the solenoid 84 in the de-energized state); etc. This logging feature can, in some embodiments, be user programmable (via the user interface 136), whereby a user can request only desired segments or types of logged information be presented, essentially filtering out all other logged information (e.g., where a clinician wants to review only information relating to attempted needle accesses to the catheter access port assembly 36 while in the closed state).

The implantable therapeutic substance delivery systems, devices and related methods of use in accordance with principles of the present invention provide a marked improvement over previous designs. In particular, the denial device consistently blocks, and permits passage to, the catheter access port over an extended period of time. In addition, a user is provided with the ability to externally control operation of the denial device in a variety of desired fashions.

Although the present invention has been described with reference to preferred embodiments, workers skilled in the art will recognize that changes can be made in form and detail without departing from the spirit and scope of the present invention.

What is claimed is:

1. A liquid therapeutic substance delivery system comprising:
    an implantable medical device for delivering a liquid therapeutic substance to a delivery site within a patient, the delivery device including:
        a housing defining a catheter outlet;
        a reservoir maintained by the housing for containing the therapeutic substance, the reservoir forming a reservoir outlet;
        a reservoir fill port fluidly connected to the reservoir;
        a catheter access port apart from the reservoir fill port and including a needle inlet defining a passage, a well fluidly coupled to the catheter outlet via a fluid pathway, and a septum disposed between the well and the needle inlet; and
        a denial device associated with the catheter access port and including:
            a pin arranged to be movable between a first position in which the pin blocks passage of a needle into the well and a second position in which the pin does not prevent passage of a needle into the well,
            a biasing element biasing the pin to the first position,
            a solenoid operatively coupled to the pin and providing an energized state and a de-energized state, the solenoid being adapted and arranged such that in the energized state, the solenoid operates to move the pin from the first position to the second position,
            wherein the well is not fluidly sealed relative to an exterior of the medical device by the pin in the first position.

2. The system of claim 1, wherein the needle inlet passage defines a central axis, and further wherein the denial device is positioned such that the pin moves laterally relative to the central axis in transitioning between the first and second positions.

3. The system of claim 1, wherein the needle inlet passage defines a central axis, and further wherein the denial device is positioned such that the pin move co-axially relative to the central axis in transitioning between the first and second positions.

4. The system of claim 1, wherein the septum defines an outer surface and an inner surface, the outer surface facing the needle inlet passage and the inner surface facing the well, and further wherein the denial device is positioned such that the pin is associated with the inner surface to block passage of a needle through the septum and into the well.

5. The system of claim 4, wherein the solenoid is vertically below the septum, opposite the needle inlet passage.

6. The system of claim 1, wherein the septum defines an outer surface and an inner surface, the outer surface facing the needle inlet passage and the inner surface facing the well, and further wherein the denial device is position such that the pin is associated with the outer surface to block passage of a needle through the needle inlet passage and into the septum.

7. The system of claim 1, wherein the denial device further includes an elastomeric seal between the pin and the solenoid to prevent passage of liquid into the solenoid.

8. The system of claim 1, wherein the denial device further includes a bellows forming a hermetic seal between the pin and the solenoid to prevent passage of liquid into the solenoid.

9. The system of claim 1, wherein the denial device further includes a welded barrier hermetically separating the pin from the solenoid.

10. The system of claim 1, wherein the implantable medical device further includes a metering device coupled to the reservoir outlet, the metering device having a metered outlet fluidly connected to the catheter outlet along a fluid pathway, and further wherein the well is fluidly coupled to the fluid pathway between the metered outlet and the catheter outlet.

11. The system of claim 1, wherein the implantable medical device further includes a device controller electronically coupled to the solenoid for selectively prompting operation of the solenoid in the energized state and the de-energized state.

12. The system of claim 11, wherein the implantable medical device further includes a telemetry device, the system further comprising:
    an external controller including a user interface and a telemetry device for communicating information to the medical device telemetry device, the external controller adapted to:
        receive information from the user interface indicative of a user intention to insert a needle into the catheter access port, and
        prompt signaling of information to the device controller indicative of the user intent;
    wherein the device controller is adapted to prompt operation of the solenoid in the energized state in response to the user intent information.

13. The system of claim 12, wherein the device controller includes a microprocessor programmed with software adapted to act upon the user intent information in controlling operation of the solenoid.

14. The system of claim 12, wherein the device controller includes a hardware based state machine adapted to act upon the user intent information in controlling operation of the solenoid.

15. The system of claim 12, wherein the implantable medical device further includes:
   a detection device associated with the catheter access port and adapted to detect presence of a needle in the catheter access port;
   wherein at least one of the device controller and the external controller is adapted to prompt operation of the solenoid based upon information from the detection device.

16. The system of claim 15, wherein the device controller is adapted to perform a catheter access port insertion routine including:
   prompting the solenoid to operate in the energized state for a predetermined time period upon receiving the user intent information; and
   prompting the solenoid to operate in the de-energized state upon expiration of the predetermined time period if the detection device information is indicative of a needle not being present in the catheter access port.

17. The system of claim 12, wherein the device controller stores a predetermined time period value and is adapted to further prompt operation of the solenoid based upon the predetermined time period value.

18. The system of claim 17, wherein the device controller is adapted to alter the stored predetermined time period value in response to instructions delivered from the external controller, the instructions being generated in response to information entered at the user interface.

19. The system of claim 12, wherein the external controller stores a predetermined time period value based upon which the solenoid is operated, the external controller being further adapted to transmit the predetermined time period value to the device controller with the user intention information.

20. The system of claim 19, wherein the external controller is adapted to alter the stored predetermined time period value in response to user instructions entered at the user interface.

21. The system of claim 12, further comprising:
   a detection device associated with the catheter access port and adapted to detect presence of a needle in the catheter access port;
   wherein at least one of the device controller and the external controller is adapted to log information relating to activities occurring relative to the catheter access port assembly, the activities including:
      the denial device in an open state and a needle insertion event is detected,
      the denial device in an open state and no needle insertion event is detected, and
      the denial device in a closed state and an attempted needle insertion event is detected.

22. The system of claim 1, wherein the pin terminates at a leading end opposite the solenoid, and further wherein relative to a central axis of the passage, the leading end is spaced from the central axis in a first direction in the first position and is spaced from the central axis in a second direction in the second position, the first and second directions being opposite of one another.

23. The system of claim 22, wherein the leading end does not physically contact the catheter access port in the first position.

* * * * *